(12) United States Patent
Tozzi et al.

(10) Patent No.: US 9,095,341 B2
(45) Date of Patent: Aug. 4, 2015

(54) MEDICAL DEVICE COMPRISING AN ARTIFICIAL CONTRACTILE STRUCTURE

(75) Inventors: Piergiorgio Tozzi, Lausanne (CH); Enzo Borghi, Budrio (IT); Daniel Hayoz, Villars-sur-Glane (CH); Martin Horst, Horw (CH); Marco Wieland, Bale (CH)

(73) Assignee: MYOPOWERS MEDICAL TECHNOLOGIES SA, Lausanne (CH)

( * ) Notice: Subject to any disclaimer, the term of this patent is extended or adjusted under 35 U.S.C. 154(b) by 162 days.

(21) Appl. No.: 13/805,453

(22) PCT Filed: Jul. 1, 2011

(86) PCT No.: PCT/EP2011/003285
§ 371 (c)(1),
(2), (4) Date: Dec. 19, 2012

(87) PCT Pub. No.: WO2012/000680
PCT Pub. Date: Jan. 5, 2012

(65) Prior Publication Data
US 2013/0096586 A1   Apr. 18, 2013

(30) Foreign Application Priority Data
Jul. 2, 2010   (EP) .................................... 10168217

(51) Int. Cl.
*A61B 17/12*   (2006.01)
*A61F 2/00*   (2006.01)
(Continued)

(52) U.S. Cl.
CPC ......... *A61B 17/12009* (2013.01); *A61F 2/0036* (2013.01); *A61M 1/1068* (2013.01);
(Continued)

(58) Field of Classification Search
CPC   A61B 17/12009; A61B 17/12; A61F 2/0036; A61F 2210/0033; A61F 2250/0001; A61F 2250/001; A61M 1/1068; A61M 1/127; A61M 1/122; A61M 1/107; A61M 1/1072; A61M 1/1086

USPC ................. 600/30, 37, 17, 16, 8, 9; 623/3.11, 623/11.11, 24, 3.1, 23.72; 417/413.1; 607/35; 606/201, 202
See application file for complete search history.

(56) References Cited

U.S. PATENT DOCUMENTS

| | | | | |
|---|---|---|---|---|
| 5,713,954 | A | * | 2/1998 | Rosenberg et al. .............. 600/17 |
| 6,099,460 | A | * | 8/2000 | Denker ............................ 600/17 |

(Continued)

FOREIGN PATENT DOCUMENTS

| | | |
|---|---|---|
| EP | 1 238 638 A1 | 9/2002 |
| JP | 7-051304 A | 2/1995 |

(Continued)

OTHER PUBLICATIONS

European Search Report, dated Nov. 10, 2010, from corresponding European application.

(Continued)

*Primary Examiner* — Jocelin Tanner
(74) *Attorney, Agent, or Firm* — Young & Thompson (57) ABSTRACT

A medical device including artificial contractile structures generally devised to be used in the medical field. Such structures may be advantageously used to assist the functioning of an organ. The medical device includes an artificial contractile structure having at least two contractile elements (100) adapted to contract an organ, in such way that each of the contractile elements (100) can be in a resting or in an activated position, independently of the position of each other, the activated position being defined with the contractile element (100) constricting the organ and the resting position being defined with the contractile element (100) not constricting the organ, and at least one actuator designed to activate the contractile structure. Each contractile element (100) is connected to an adjacent contractile element (100), while remaining flexible one with respect to the other.

24 Claims, 6 Drawing Sheets

(51) Int. Cl.
*A61M 1/10* (2006.01)
*A61M 1/12* (2006.01)

(52) U.S. Cl.
CPC ....... *A61M 1/122* (2014.02); *A61F 2210/0033* (2013.01); *A61F 2250/001* (2013.01); *A61F 2250/0001* (2013.01); *A61M 1/127* (2013.01)

(56) References Cited

U.S. PATENT DOCUMENTS

| | | | |
|---|---|---|---|
| 6,592,619 B2* | 7/2003 | Melvin | 623/3.11 |
| 2005/0148814 A1* | 7/2005 | Fischi et al. | 600/37 |
| 2007/0156013 A1* | 7/2007 | Birk | 600/37 |
| 2010/0204803 A1* | 8/2010 | Tozzi et al. | 623/23.72 |

FOREIGN PATENT DOCUMENTS

| | | |
|---|---|---|
| WO | 2007/066344 A1 | 6/2007 |
| WO | 2009/004092 A1 | 1/2009 |
| WO | 2009/048399 A1 | 4/2009 |
| WO | 2009/127427 A1 | 10/2009 |

OTHER PUBLICATIONS

International Search Report, dated Dec. 5, 2011, from corresponding PCT application.

H. Emoto et al., "Systemic and local effects of heat dissipation in the thermally powered LVAS", ASAIO Trans., Jul.-Sep. 1988, pp. 361-366, vol. 34, No. 3, Abstract only.

* cited by examiner

MEDICAL DEVICE COMPRISING AN ARTIFICIAL CONTRACTILE STRUCTURE

TECHNICAL FIELD

The present invention relates to a medical device comprising an artificial contractile structure activated by an actuator, which may be advantageously used to assist the functioning of an organ, e.g. a sphincter or the heart. More generally, it can be used for moving or constricting a hollow or a tubular part of the body in such a way as to reduce its diameter.

BACKGROUND OF THE INVENTION

It is known to use artificial structures to assist muscular contraction. Such structures are adapted to assist atrial or ventricular contraction, or to assist or replace a natural sphincter. The use of such artificial sphincters has increased in recent years because faecal and urinary incontinences now affects more than 10% of people over 60 years of age and dramatically increases in patients over 80 years of age. Several pharmaceutical or surgical solutions have been developed for treating urinary and faecal incontinences. Generally, the outcome of surgery for treatment of urinary and faecal incontinence has to be regarded as low. The impacts on health care costs and overall quality of life of the patient are enormous.

The AMS800 artificial sphincter for urinary incontinence is commercialized by American Medical Systems and is composed of three components, a cuff, a pump, and a pressure-regulating balloon. The cuff is implanted at the bulbous urethra in males and is inflatable by means of a fluid. The pump is implanted in the scrotum and the pressure-regulating balloon is implanted in the abdomen. The major problems when using AMS800 is the tissue erosion around the urethra due to the constant pressure, the atrophy and irritation of tissues at the location of the inflatable cuff, and the emergency surgery for repair should the device remain in closed position in the event of mechanical failure. All other commercialized artificial sphincters whether for urinary or faecal incontinence bear similar drawbacks.

The ProAct™ artificial sphincter for urinary incontinence is commercialized by Uromedica and is composed of two small implantable balloons. During a short outpatient procedure, the balloons are surgically placed under the skin in the area where the prostate of the patient was surgically treated. The balloons help protect against accidental leaking of urine by increasing the amount of pressure required to urinate. When the patient needs to urinate, a normal amount of effort still should be required to push the urine out. However, the pressure from the balloons will help guard against unintentional urine loss, such as during a sneeze or cough. The major problems when using ProACT™ are identical to the problems using AMS800 artificial sphincter described above.

FlowSecure™, manufactured by Sterilin Ltd, another silicone hydraulic urinary sphincter similar to AMS800, has an extra pressure transmission balloon to transfer increased intra abdominal pressure directly to the cuff. Implantation of this device is technically feasible, but still difficult and is reported to be safe and effective in the short-term for the treatment of male urodynamic stress urinary incontinence, arising from a number of etiologies. However, the major problems when using FlowSecuren™ are identical to the problems using AMS800 artificial sphincter described above.

Some publications describe the use of artificial sphincters comprising shape memory alloy elements suitable for opening and closing a part of an organ in a living body. EP 1 238 638 describes an artificial sphincter having an opening/closing portion for opening and closing, wherein said opening/closing portion has:
 a pair of elongated shape memory alloy elements that change reversibly between opposite shapes upon changes in temperature, and
 hinges that link said pair of shape memory alloy elements together in a cylindrical shape.

Such artificial sphincter is placed around the intestine of a human or animal inside the body near to an intestinal opening so that the opening/closing portion constricts the intestine. When the shape memory alloy elements are heated, they change shape, so that the constricting force on the intestine is lost.

However, as the opening/closing portion is still constricting the same region of the intestine, there is likely damage to this part of the body, and more especially a risk of tissue erosion, atrophy and burns, due to the constant pressure and heating of the shape memory alloy elements.

Reversible thermal lesions occur when the local temperature is increased to the 42° C. to 44° C. range (5 C-7° C. over the normal body temperature of 37° C.) and that irreversible thermal lesions occur when the local temperature is increased above 45° C. (>8° C. temperature rise over 37° C., which is the normal temperature). The time over overheating also plays an important role.

Moreover, in normal state, the shape memory alloy elements are not heated and are each bent to constrict the intestine. That means that heating is necessary to open the artificial sphincter. If the heating means fail, the sphincter remains closed and cannot be opened, what may be leading to life threatening complications. An emergency surgery is then necessary to open the artificial sphincter and to solve the problem.

Another artificial sphincter has been proposed in JP 07-051304. This document describes a constrictor comprising two shape memory alloy elements with different shape memories, and covered by covering materials.

The first covering material is formed in a shape to close the urethra in the daytime, and the second covering material is formed in a shape to half close the urethra in the night. This sphincter allows changing the pressure to the urethra, in order to prevent the incontinence in life action in the daytime, and to avoid necrosis of the tissue by loosing the pressure to the urethra in the night. If the shape memory alloy is no more efficient or is broken, the whole sphincter should be moved and replaced.

However, the drawbacks of such artificial sphincters are that there is a risk of tissue erosion and consequential necrosis, due to the high constant pressure to the urethra during the day and that there is a risk of incontinence during the night.

Moreover, JP 07-051304 discloses an artificial sphincter in which the shape memory alloy elements are disconnected from each other. This embodiment does not allow optimal pressure control.

Moreover, this kind of shape memory alloy elements uses a lot of power. That means that the battery needs to be changed very often or alternatively very large batteries have to be used.

Other medical devices comprising contractile element are known.

WO 2009/004092 discloses an artificial structure comprising several contractile elements adapted to contract an organ. But the contractile elements are connected to a support which is not flexible, in such a way that the contractile elements are not flexible one with respect to the other.

WO 2009/0048399 discloses an apparatus for controlling a flow of sperms in an uterine tube, comprising an implantable flow influence device to be applied on at least one portion of the uterine tube. The constriction device may comprise a clamping element, two clamping elements radially movable, an elongated circular constriction member or elastic strings interconnecting two annular holders. But this document does not disclose any contractile elements designed to contracting at least two portions of an organ, connected to a support and flexible along the uterine tube one with respect to the other.

WO 2007/066344 discloses an implantable extra cardiac compression device for left ventricular assistance in severe heart failure. The device comprises metal flanges that are passively flexed at springed-hinges by a vertically moving metal cup. The vertical movements of the metal cup are achieved by means, such as a motor driven rack-and-pinion mechanism, or, a linear induction motor system. The flanges are connected to each other by a high-tensile, elastic polymer membrane. However, with such device, the flanges are all in the same position, activated or not. As the flanges are moved by the moving of the cup, one flange cannot be in an activated position while the other flanges are in the resting position. Furthermore, one flange, used alone, cannot contract the organ.

US 2005/148814 discloses a device for assisting a heart comprising a carrier having a plurality of mutually interconnected electrically operated actuators, designed to compress at least a portion of the heart. In such device, one actuator, used alone, is not able to contract the organ.

WO 2009/127427 discloses a pressure device designed to be placed outside the body, and comprising several pressure segments able to apply a pressure on the body. The device discloses in this document is not implantable for contracting an internal organ. Furthermore, the pressure segments are not able to contract the portion of organ in such a way that said portion is closed.

Therefore there are, at the present time, no adequate solutions, whether commercial or in the literature, for implanting device comprising an artificial contractile structure, particularly for the treatment of faecal or urinary, incontinence.

SUMMARY OF THE INVENTION

The present invention provides a medical device comprising an artificial contractile structure which allows to avoid the disadvantages of the prior art.

Accordingly, the present invention relates to a medical device comprising:
an implantable artificial contractile structure comprising at least two contractile elements adapted to contract an organ, in such way that each of said contractile elements can be in a resting or in an activated position, independently of the position of each other, the activated position being defined with said contractile element constricting the organ and the resting position being defined with said contractile element not constricting the organ,
at least one actuator designed to activate said contractile structure.

According to the invention, each contractile element is connected to an adjacent contractile element, while remaining flexible one with respect to the other. Each contractile element is able to contract a portion of the organ and to be activated or in a resting position independently of the position of the other contractile elements.

In some embodiments, the medical device may comprise at least two actuators, each of said actuators being associated with one of said contractile elements and designed to activate said associated contractile element. Each actuator may comprise fibers made of a contractile material and fixed to each of said contractile elements.

In some embodiments, said actuator may be separated from the artificial contractile structure, said actuator further comprising transmission means linked to the contractile elements and designed to transmit to the contractile elements a force induced by the actuator.

In some embodiments, said actuator may comprise at least one fiber made of a contractile material and linked to said transmission means, which are designed to transmit to the contractile elements a force induced by at least one contraction of the fiber.

In other embodiments, said actuator may comprise at least one electromotor linked to said transmission means, which are designed to transmit to the contractile elements a force induced by said electromotor.

Said transmission means may be mechanical, hydraulic, electromechanical or pneumatic. For example, the mechanical transmissions means may be cables linking the actuator to the contractile elements.

"Each contractile element is connected to an adjacent contractile element" means that an independent contractile element and its adjacent independent contractile element are physically linked or connected to each other, directly or indirectly, by an appropriate connecting element, allowing an appropriate compromise between the stiffness and the flexibility of the structure. The structure of the invention allows applying minimal pressure to the tissues thereby avoiding tissue necrosis and damage. Moreover, the present invention allows optimal pressure control and implantation of the structure by surgeons, by having a single-piece device which is adaptive to the natural flexibility of the urethra while remaining semi-rigid so that the structure stays in place and the pressure of each element can be optimally synchronized.

Advantageously, the contractile elements are each flexible so that each has the freedom to move longitudinally no more than 5 mm to each direction, preferably no more than 3 mm to each direction, and more preferably no more than 1 mm to each direction from an adjacent contractile element and so that it can move according to a transversal rotation no more than 30°, to each side preferably no more than 20° to each side from an adjacent contractile element.

In some embodiments, the medical device according to the invention may further comprise a first flexible connecting element designed to link each contractile element to an adjacent contractile element, said connecting element being made out of elastic biocompatible material for keeping said contractile elements in longitudinal position while allowing a rotational movement of each contractile element one with respect to the other. Such first flexible connecting element may be fastened directly to the connecting element.

In other embodiments, two adjacent transmissions means are merged in such a way that the two corresponding adjacent contractile elements are indirectly connected.

In some embodiments, the medical device further comprises at least one second connecting element designed to merge the adjacent transmissions means of two adjacent contractile elements, in such a way that said adjacent contractile elements are indirectly connected via their transmissions means, and more particularly via the cables linking the actuators to the adjacent contractile elements. In other embodiments, the transmissions means may be merged by overmolding. In this manner, the contractile elements may be kept in longitudinal position while allowing a rotational movement of each contractile element one with respect to the other.

Advantageously, the contractile element may have a diameter comprised between 8 mm and 35 mm, when it is closed. The dimensions of the contractile element are such that, when they are fully open, the surgeon can move an endoscope through the lumen of the urethra/rectum in order to endoscopically examine the patient or kidney stone removal is possible.

Advantageously, said contractile element is each separated from an adjacent contractile element no less than 1 mm to 2 cm, preferably 2 mm to 1 cm, more preferably 2 mm to 8 mm, for avoiding over-compression.

In some embodiments, the artificial contractile structure may comprise between 2 and 8 contractile elements, so that said structure makes an overall length comprised between 20 mm and 50 mm.

In some embodiments, the medical device according to the invention may further comprise a control unit which is adapted to activate the actuator in such a way that each contractile element is activated pulsatory and alternately relating to the other contractile elements.

In a preferred embodiment, the actuator may be designed so that the contractile element applies, in a pulsating and alternating manner, a pressure on an organ to be contracted during a period comprised between 30 seconds and 90 minutes, preferably between 30 seconds and 60 minutes, preferably between 30 seconds and 45 minutes, and more preferably between 10 minutes and 30 minutes. Preferably, the strength is such that the different regions of the organ are completely closed in a pulsating and alternating manner.

Moreover, the medical device according to the invention may further comprise a source of energy.

In some embodiments, the source of energy may comprise at least one implantable rechargeable battery with an implantable antenna and an external battery.

In other embodiments, the source of energy may be at least one implantable primary battery.

Advantageously, the present invention provides an artificial medical device which is designed for chronic applications (i.e. long-term implantation), for example for many months and preferably many years.

Such medical device may be used in several indications, e.g. for assisting or replacing a natural sphincter, especially for the treatment of faecal or urinary incontinence, for assisting atrial or ventricular contraction, for assisting the respiratory function, for assisting or replacing a paralyzed muscle or for treating venous insufficiency. The present invention is particularly designed for improving sphincter muscle function and therefore to improve the patient's quality of life with a significant reduction of treatment costs.

DETAILED DESCRIPTION

In the present description, the term "organ" covers any organ of the human body, preferably an organ comprising a hollow part, containing fluids as for example the ventricular part of the heart, or a region of an organ in the living body having an overall cylindrical shape, for example a blood vessel, the urinary tract, the colon, the stomach or any other body part against which pressure can be applied.

In the present description, the term "electromotor" covers any device designed to produce motion and mechanical effects by the action of electricity.

In the present description, the term "constrict" means that the contractile element applies a pressure against a region of an organ around or on which said contractile element has been placed.

In the present description, the term "pulsatory" means that each contractile element is activated and deactivated in alternation with another contractile element to constrict or apply a pressure or not against the region of the organ or the hollow part of the organ around or on which it has been placed, preferably so as to close or open said region of the organ or of the hollow part. More especially, in a preferred embodiment, contractile element one is closed for a certain time while the other contractile element(s) are open. After a given time the contractile element two will be closed while the contractile element one is still closed. When contractile element two is closed, contractile element one opens, and so on. The frequency of alternate activation is dependent upon the nature of the tissues and inside organ pressure, and is adjusted so that no tissue erosion and burn appear after several months of implantation.

In the present description, the term "link" means a direct or indirect connection between two elements.

In first embodiments of the invention, the actuator comprises fibers made of a contractile material. In the present description, the term "contractile material" means in particular Electro Active Polymers (EAP), Electro Active Ceramics (EAC), Shape Memory Alloys (SMA). Any suitable material can be used for the fibers. A suitable SMA material for the contractible fibers is for example Nitinol™. In this case the fibers can be stretched by as much as 4% when below the transition temperature, and when heated, they contract, recovering thereby to their original, shorter length with a usable amount of force in the process. The mechanical characteristics are a function of the chemical composition and thermal processing. The transition temperature range varies according to the fiber's chemical composition and is usually comprised between 35° C. to 90° C. for applications such as implantable devices, stents, implantable active devices, surgical and orthopedic tools and electrical and thermal actuators. The Nitinol consists of about 50% Ni and 50% Ti. Such Nitinol wires and fibers are commercialized e.g. by Memry.

The fibers can have a spiral form in order to increase the length of the shortening.

Other particularly interesting materials are Biometal fibers (BMF) commercialized by Toki Corporation Inc., Japan (for example fibers BMX150 or BMF100). Those materials are able to reversibly contract upon a controlled heating caused by the supply of an electric current/voltage and can be repeatedly used several thousands of millions of times.

Such fibers are made for example of Ni—Ti—Cu alloy. For example, the composition ratios of Ni, Ti, and Cu are 46.9%, 44.8%, and 8.3%, respectively.

The fibers can also be part of the contractile elements. In some embodiments, the contractile element may comprise two separate parts, said fibers may be designed to be fixed to the first part and to the second part of the contractile element in such a way that said first and said second parts come closer to each other when said fibers are contracted, in order to be able to reduce the volume of the organ to be contracted.

In another embodiment, the contractile element is a band which surrounds at least one time the hollow part of the organ to be contracted in such a way that the ends of the band overlap each other. The fiber is designed to be fixed to a first and a second zone of the band, in such a way that, when the band is rolled, the fiber crosses the overlap zone to close it, and when the fiber is contracted, one end of the band slides over the other end of said band.

Each fiber may be thermally insulated in such a way that the temperature of said fiber does not decrease by more than 10° C., preferably 8° C., more preferably 5° C. compared with the transition temperature of the fiber, when the fiber is not contracted.

The insulation of each fiber with a matrix designed to maintain the temperature of the fibers slightly below the transition temperature between the martensite and the austenite states, allows to better control the contractibility of the fibers and therefore is significantly reducing the energy consumption for the same contraction efficacy.

Moreover, the fibers may be covered or coated by an insulating substance to provide thermo-insulation of the structure thereby reducing the risk of lesions of the surface of the organ to be contracted.

Advantageously, each fiber is independently covered or coated by a thermally insulating biocompatible and elastic material which has a thickness comprised between 10 µm and 500 µm, preferably between 10 µm and 200 µm, more preferably between 10 µm and 100 µm.

Preferably said thermally insulating biocompatible and elastic material is selected from the group consisting of biocompatible silicone, polylactide (PLA)-polymer, polyurethane (PUR), polytetrafluorethylen (PTFE), Polymethylmethacrylate (PMMA), polyoxymethylene (POM), HDPE polyethylene, LDPE polyethylene and combination thereof. Other appropriate material can be used.

Advantageously, the fibers are designed in such a way that the temperature of fluids or tissues surrounding said organ does not increase above 40° C., preferably 39° C., and more preferably 38° C.

It has been found that the control of temperature is a significant parameter for avoiding tissue necrosis and tissue erosion, and surprisingly that less than 3° C., preferably less than 2° C., and more preferably less than 1° C., over the normal human body temperature (of 37° C.), is particularly protective of the tissue surrounding, and this irrespective of the shape and nature of the contractile-powered structure. This is particularly surprising as a temperature increase of 7° C. to 8° C. over the normal body temperature of 37° C. is not known to create tissue lesions (Hemoto H et al. Systemic and local effects of heat dissipation in the thermally powered LVAS. ASAIO trans. 1988 July-September; 34(3):316-6).

In other embodiments, the fibers can be also separated from the contractile elements, said contractile elements being designed to be activated by transmission means linking the fibers to the contractile elements of the structure, as cables linking the fibers to the contractile elements. Said cables may be protected by a coaxial sheath. The sheath can be made for example of silicone, polyimide, PTFE composites (PTFE and fluoroethylkene polymers), pure PTFE, or other appropriate polymers. The sheath can be additionally coated with silicone, if necessary. The cables themselves can be made for example out of polyamide like Nylon®, polyether block amide, PTFE, or other appropriate polymers. Alternatively, other materials, as stainless steel or titanium, can be used. One end of the cable may be connected liquid tight to the corresponding contractile element of the structure and the other end of the cable is linked liquid tight to the fibers. In the present description, the terms "liquid tight" means liquid tight also humidity tight or hermetic sealed. Moreover, in some embodiments, one end of the cable may be reversibly connected to the corresponding contractile element of the structure and the other end of the cable may be reversibly linked to the fibers in such a way that the cable may be separated from the contractile element or from the fibers.

The fibers can be placed in a closed box away from the organ to be contracted. The distance between the box and the organ is comprised between 3 cm and 40 cm.

The fibers may be used in an actuator comprising an oscillating device designed to have a movement inducing oscillations under the effect of repeated contractions of the fibers, the transmission means being designed to be able to convert one or more oscillations of the oscillating device into one or more cumulative contracting movements generating one or more cumulative contracting forces transmitted to the contractile element in such a way that said contractile element reaches its activated position. Said transmission means further comprise releasing means designed to allow a return of the contractile element to its resting position, so that the activated position of said contractile element is able to be reached more than only one time.

If contractile fibers are used for inducing the oscillations of the oscillating device, such fibers may generate an oscillation comprised between 2 times/min and 30 times/min with a magnitude comprised between 0.1 mm and 25 mm.

Moreover, the activated position of the contractile element may be reached with one or more cumulative contractions corresponding to a global contraction of the contractile element having a magnitude comprised between 0.2 mm and 50 mm.

Each of said transmission means may further comprise:
pushing means provided on the oscillating device,
a mobile element linked to the contractile element and slidably mounted on a supporting part from an initial position, said mobile element being designed to cooperate with the pushing means in such a way that, at each oscillation, the pushing means pushes the mobile element in a direction inducing one contraction of said contractile element,
retaining means designed to cooperate with the mobile element and to prevent said mobile element from going back in an opposite direction.

Preferably, the pushing means comprise a pushing strip attached to the oscillating device, and the mobile element is a toothed element, as a rack, linked to the contractile element, said toothed element being designed to cooperate with the pushing strip in such a way that, at each oscillation, the pushing strip pushes the toothed element in the direction inducing one contraction of the contractile element.

Advantageously, the retaining means are a jumper spring designed to cooperate with the mobile element.

Preferably, said releasing means are designed to separate the pushing means and the retaining means from the mobile element in such a way that the mobile element comes back into its initial position.

The supporting part is able to move away from the pushing strip and the retaining means and said releasing means are designed to move the supporting part away from the pushing strip and the retaining means when the mobile element has to come back into its initial position.

Said releasing means are fibers made of a contractile material which contracts when heated, in order to pull on the supporting part and move it away from the pushing strip and the retaining means.

Each actuator further comprises sensors designed to indicate the position of the mobile element to the control unit.

Such specific actuator can be used separately for another application and can be considered as independent of the present invention.

Each of said transmission means further comprise a transmission element linking the mobile element to the contractile element, said transmission element being designed to transmit to said contractile element the contracting movement induced by the oscillations of the oscillating device, and said contractile element is designed to reach its activated position when said contracting movement induced by the oscillations of the oscillating device is transmitted by the transmission element to said contractile element. Preferably, the transmission element may be a cable linking the mobile element of the actuator to the contractile independent element.

If the fibers have been moved away from the organ to be contracted, the present invention avoids the damage of the tissue due to the increase of the temperature of the fibers. The invention allows also replacement of the fibers more easily if necessary. Moreover, the fibers can be placed in the same box as the control unit and the source of energy. There is therefore no problem of electric insulation. Advantageously, especially if the fibers are placed in a second box, the thermal insulation can be obtained and the temperature decrease is limited. This allows also to a decrease in power consumption. The fibers can be used in a straight position and in the form of wire. This has the advantage of lowering the power consumption and increasing the battery life time.

Moreover, if the apparatus of the invention comprises the specific actuator as described above, in which the contractile fibers activate a toothed element, the power consumption can be significantly reduced. Indeed, the fibers need to be activated only until the toothed element is in its final position corresponding for example to the activated position of the contractile element. As the toothed element is maintained by the retaining means, the fibers do not need to be activated to maintain said contractile element in its activated position. Therefore, the fibers of the actuator need power only to close and open the contractile element. The time to close the contractile element is for example about 1 minute for a urinary device and the time to open less than 1 second. In terms of a 5 minutes cycle, power is needed for about 1 minute instead of 5 minutes if the fibers need to be activated to maintain the contractile element in its activated position during 5 minutes. Such embodiment allows an increase in the battery life time.

In a second embodiment of the invention, the actuator comprises at least one electromotor linked to said transmission means, which are designed to transmit to the contractile elements a force induced by said electromotor. This actuator is separated from the contractile structure. That means that the actuator is not fastened on the contractile structure or on the contractile element. In a preferred embodiment, said electromotor may comprise an electric motor, a gearhead connected to said motor, a lead screw cooperating with said gearhead, and a nut mounted on said lead screw and linked to said transmissions means. The actuator may further comprise sensors designed to indicate the position of the nut or the force applied by the actuator.

In this embodiment, the transmission means may preferably be cables protected by a coaxial sheath. The sheath can be made for example of silicone, polyimide, PTFE composites (PTFE and fluoroethylkene polymers), pure PTFE, or other appropriate polymers. The sheath can be additionally coated with silicone, if necessary. Sheaths and cables are well known in surgery. The cables can be made for example out of polyamide like Nylon®, polyether block amide, PTFE, or other appropriate polymers. Alternatively, other materials, as stainless steel or titanium, can be used. Surgeon is used to place cables in the human body. One end of the cable may be connected liquid tight to the contractile element and the other end of the cable is linked liquid tight to the nut of the actuator. Moreover, in some embodiments, one end of the cable may be reversibly connected to the contractile element and the other end of the cable may be reversibly linked to the nut of the actuator in such a way that the cable may be separated from the contractile element or from the actuator. In some embodiments both ends of the cable are irreversible connected to the contractile element and nut, respectively and molded with silicone to become liquid tight.

In some embodiments, two adjacent transmission means, as cables, of two adjacent contractile elements may be connected by bars or other similar connecting elements used to merge said two adjacent transmission means. In other embodiments, the two adjacent transmission means may be connected by overmolding them with silicone. In these both cases, the two adjacent contractile elements corresponding to the two adjacent transmission means are connected indirectly, while remaining flexible one with respect to the other.

In this embodiment, when energy is provided to the electromotor, this energy is transmitted directly to the lead screw which converts its rotative movement to a lateral movement of the nut. When the nut moves along the lead screw, it pulls or pushes on the cable to close or open the contractile element. No extra release mechanism is required. No or minimal energy is needed to maintain the contractile element in its activated position, which means that the maximum pressure on the organ is maintained with minimal energy consumption. In the case corresponding to minimal energy consumption, only a few electronic components are permanently powered.

Most energy is needed for just a few seconds to move the nut and close or open the contractile element. Then, the power consumption can be significantly reduced, that allows an increase in the battery life time.

That means that the ratio "current which is needed to maintain the contractile element in its activated position/current which is needed to change the position of the contractile element" is comprised between 1/20000 and 1/500, preferably between 1/14000 and 1/800, and more preferably between 1/8000 and 1/1000.

More particularly, the motor, the gear ratio and the lead screw have been chosen in such a way that the energy consumption of the medical device is comprised between 50 mAh/year and 2 000 mAh/year for a pressure applied by the contractile elements on the organ comprised between 0.1 N/cm$^2$ and N/cm$^2$, preferably through the pulsatory contracting. Preferably, the energy consumption of the medical device is comprised between 70 mAh/year and 1 500 mAh/year for a pressure applied by the contractile elements on the organ comprised between 0.3 N/cm² and 2.5 N/cm², preferably through the pulsatory contracting.

More particularly, the current consumption of the medical device of the invention which is needed to change the position of the contractile element for five years is comprised between 350 mAh and 9000 mAh, preferably between 350 mAh and 6750 mAh, and the current consumption of said medical device which is needed to maintain the contractile element in its activated position is comprised between 150 mAh and 1000 mAh for a continuous, and preferably alternative, pressure applied on the organ by the contractile element, which is in its activated position, comprised between 0.1 N/cm² and 5 N/cm², preferably between 0.3 N/cm² and 2.5 N/cm².

With such lower energy consumption, the operation time of the battery used as source of energy is comprised between 1 year and 10 years, preferably between 2 years and 8 years, optimally at least 5 years, for a battery having a volume of 3 cm³ to 20 cm³.

The medical device of the invention allows therefore the use of a least one primary battery placed inside the body of the patient, which is to be changed only several years after its implantation, optimally at least 5 years.

Moreover, the motor, the gear ratio and the lead screw have been chosen in such a way that the travel time needed by the nut for moving along the lead screw between the resting position and the activated position is comprised between 0.2 s and 90 s, for a travel of the nut comprised between 2 mm and 50 mm, preferably between 3 mm and 15 mm. Preferably, the travel time needed by the nut for moving between the resting position and the activated position is comprised between 0.4 s and 60 s, more preferably between 0.5 s and 10 s, and more preferably between 0.5 s and 5 s for a travel of the nut comprised between 2 mm and 50 mm, preferably between 3 mm and 15 mm.

The time for opening or closing the contractile element could be different and depends on the material of the contractile element.

The appropriate electromotor is commercialized for example by Maxon Motor AG, Faulhaber or Portescap. Preferably, the gear ratio is comprised between 4 and 64, and preferably between 16 and 64. The lead screw has a pitch comprised between 1 and 3 and an effective diameter comprised between 2 mm and 4 mm.

The medical device of the invention can be used with different embodiments of actuators. The medical device can comprise only one actuator, the transmission means being designed to transmit the forces induced by the actuator to each of the contractile elements of the structure. In other embodiments, the medical device can comprise several actuators, each actuator being associated, via appropriate transmission means, to one or several contractile elements. Preferably, the actuators are controlled by the same control unit.

In the invention, the contractile structure is the contractile device which is placed around an organ to be contracted. It comprises more contractile elements disposed around the organ.

In preferred embodiments for which the actuator is separated from the artificial contractile structure, each contractile element may comprise a band which surrounds at least partially the organ to be contracted, the transmission means being designed to be fixed to one end of the band and to pull it in such a way that the band constricts the organ when the force induced by the actuator and transmitted by the transmission means is applied on said contractile element.

In a preferred embodiment, the band may comprise at one end a point for fixing the transmission means and at the other end a hole crossed by the transmission means.

In preferred embodiments, the size of the band may be comprised between 4 cm and 15 cm in length, preferably between 4 cm and 12 cm in length, and between 3 mm and 15 mm in width, preferably between 3 mm and 12 mm in width.

Preferably, the contractile element is made out of biocompatible materials. The biocompatible material is preferably selected from the group consisting of silicone and polytetrafluorethylene (PTFE), polylactide (PLA)-polymer, polyurethane (PUR), Polymethylmethacrylate (PMMA), polyoxymethylene (POM), HDPE polyethylene, LDPE polyethylene and combinations thereof. Other appropriate polymers or material, such as metal, can be used.

In the device of the invention, the actuator is controlled by a control unit, said control unit being advantageously adapted to pulsatory and alternately contract the contractile elements.

The medical device comprises also a source of energy.

The control unit and the source of energy can be implantable or placed outside the body of the patient. In a preferred embodiment, the control unit and the source of energy are implantable. The control unit and the source of energy can be integrated in the same box. The control unit and the source of energy can be also separated in two boxes (control unit and power supply unit) and connected with an electric cable (called lead cable), which should be easily detachable at least at one unit (either the control unit or power supply unit).

In other embodiments, the control unit can be implantable and the source of energy is placed outside the body of the patient. In other embodiments, both control unit and source of energy are placed outside the body of the patient.

In some embodiments, the implantable source of energy is a transcutaneously rechargeable battery. Such battery is for example a Lithium-Ion or Lithium Polymer rechargeable battery commercialized by GreatBatch and others. In this case, the medical device further comprises an energy transfer system that is needed to recharge the battery, preferably through wireless connection. Such system can comprise a recharge unit, as a belt, comprising an external battery. The patient should wear the recharge unit for a number of hours to recharge the implanted battery. The energy should be transmitted wireless to the implanted battery via appropriate antenna. The system can also comprise a cradle for charging the recharge unit. Charging can be performed through a wired or metal contact connection. The battery provides sufficient energy for at least 1 month operation of the medical device. Recharge time is less than 6 hours. In another preferred embodiment, the source of energy is at least one implantable primary (i.e. non-rechargeable) battery, having a lifetime of at least 4 years for a size of 3.7 cm3, two batteries being preferably used. The battery may be a lithium-manganese dioxide battery.

The features of the battery depend on the application of the artificial structure, on the pressure to be applied, the number of contractile elements to contract and how often the patient opens and closes the contractile elements.

If fibers made of contractile material are used in the actuator, by selecting the length, the diameter and the shape of the fibers, the device of the invention may be designed so that the required average power to supply by the source of energy is less than 3 W, preferably less than 1 W, more preferably less than 0.5 W and the maximum instantaneous power is less than 8 W, preferably less than 6 W. The maximum power can be supplied during 5 seconds only. The required voltage is dependent on the application. For example, the voltage may be less than 6 V for a urinary sphincter, and is preferably comprised between 3 V and 5 V. For a faecal sphincter, the voltage may be less than 40 V, and is preferably comprised between 17 V and 35 V.

Preferably, the devices of the invention are operated in such a manner as not to increase the temperature of surrounding fluids or tissues by more than 3° C., preferably 2° C., more preferably 1° C., as it may be measured by any body-like fluids with a temperature probe that is placed for the temperature measurement at location where the induced heating is expected to be greatest, and preferably no more distant than 5 mm away from the device.

A specific test method is also described in the norm ASTM F2182-02a. Accordingly, the artificial sphincter is placed in a gel material phantom that simulates the electrical and thermal properties of the human body. The artificial sphincter is placed within the gel phantom with its receiving antenna below the gel surface. The control unit's external antenna for application of RF power and for transmitting of data is also positioned within the gel below the receiving antenna. The phantom material includes saline solution. Fiber optic temperature probes are placed for the temperature measurements at locations where the induced heating is expected to be greatest. The phantom is placed in the structures or apparatus of the invention with a cylindrical bore. An RF field should be applied with at least 1 W/kg averaged over the volume of the phantom. The temperature rise at the sensors is measured prior, during and after the RF application of approximately 15 minutes, or other appropriate period, depending on the mass and thermal conductivity of critical parts of the device. Temperature measurements at one or more locations away from the device serve as control.

The control unit and/or power supply unit includes electronics and software designed to:
 control and adjust the actuator generating the force transmitted to the contractile element
 provide control of the actuator from outside the body through wireless connection
 optionally recharge the internal battery through wireless connection
 control the status of the battery
 provide test and diagnosis support for health care professionals
 handling of alarm conditions and exceptions.

If fibers made of contractile material are used in the actuator and are pulsatory and alternately contracted, the control unit comprises a microprocessor that distributes current to fibers so that the fibers contract pulsatory and alternately, at the required pressure and at the required frequency.

In such case, the microprocessor is designed to generate micropulses having duration lower than 100 ms, preferably comprised between 5 ms and 50 ms, more preferably between 10 ms and 20 ms and a power, which progressively increases, until the required length of the fiber is achieved. The duration between each pulse may be comprised between 5 ms and 50 ms, preferably between 5 ms and 10 ms. For example, the duration of the pulse may be 10 ms and the duration between each pulse may be 5 ms.

Moreover, the microprocessor may be designed to have a continuous feedback on the resistance of the fiber, which depends on the length of the fiber, in order to adapt the control according to the resistance of the fiber. Therefore, the apparatus of the invention is able to monitor itself, and can be used without a sensor, which is a substantial advantage to further prevent tissue damages.

The microprocessor is designed to control the proper functioning of the device.

The microprocessor can be adjusted individually for each patient regarding pressure and frequency of opening and closing.

Ideally these adjustments can be done after implantation transcutaneously, preferably by a medicinal physician in order to optimize control of volume reduction (such as incontinence leaking). Readjustments can be performed at any time during the life time of the device using a remote control, as described below.

The number of contractile elements to contract can be adapted to the required pressure to apply on the organ. For example, in the case of urinary sphincter, the number of contractile elements to open and close can be adapted to the abdominal pressure.

The pressure of the structure on the region of the organ to be contracted may be comprised between 0.1 N/cm$^2$ and 5 N/cm$^2$ and preferably between 0.3 N/cm$^2$ and 2.5 N/cm$^2$. In a preferred embodiment, the medical device of the invention comprises:
 i) an artificial contractile structure implantable into the human body and comprising at least two contractile elements, such as the contractile elements described above,
 ii) at least one actuator which upon activation will induce a contraction of the contractile elements, such as the actuators described above, wherein the actuator and the contractile elements are designed to apply a pressure on an organ to be contracted, which is comprised between 0.1 N/cm$^2$ and 5 N/cm$^2$ and preferably between 0.3 N/cm$^2$ and 2.5 N/cm$^2$, during a period comprised between 30 seconds and 90 minutes, preferably between 30 seconds and 60 minutes, preferably between 30 seconds and 45 minutes, and more preferably between 10 minutes and 30 minutes.

Each contractile element is preferably activated or deactivated several times a day, and most preferably several times an hour. The contractile elements may be activated, in a pulsating and alternating manner, during a period comprised between 30 seconds and 90 minutes, preferably between 30 seconds and 60 minutes, preferably between 30 seconds and 45 minutes, and more preferably between 10 minutes and 30 minutes. The relaxation time is dependent on the number of regions which are to be contracted by the contractile elements.

If the artificial structure is adapted to contract for example four regions of an organ, and if only one contractile element is activated at the same time, each contractile element can be activated during one minute and deactivated during three minutes in an alternating manner. In another embodiment, each contractile element can be activated during five minutes and deactivated during fifteen minutes in an alternating manner. If the structure is adapted to contract three regions of an organ, each contractile element can be activated during one minute and deactivated during two minutes in an alternating manner. If the structure is adapted to contract two regions of an organ, it comprises two contractile elements, which can be activated during 30 minutes and deactivated during 30 minutes in an alternating manner.

The activation of each contractile element can be random or sequential.

Only one of the contractile elements or several contractile elements can be contracted at the same time. In other embodiments, one contractile element can remain contracted or closed whereas another contractile element is contracted or closed.

If the patient wishes to do sport, several or all the contractile elements may be closed in such a way that the pressure, which is applied on the organ to be contracted, is increased for a certain time, typically 1 h. After that time the system goes back into the alternately activation controlled by the control unit.

To avoid tissue damage sports mode can't be activated more than twice in a raw and not more than maximum 3 hours a day.

Advantageously, the control unit is designed so that at least two contractile elements are able to be maintained in their resting position at the same time.

During the night, several or all the contractile elements may be maintained in a resting position, without any contraction in such a way that the energy consumption is reduced.

All these embodiments are obtained by means of an adequate control unit. Said control unit is designed to allow an adjustment of the pressure of the contractile structure on the organ according to the patient's need, by adjusting the force generated by the actuator. Advantage is that the physician can customize the optimal pressure of the contractile structure to side effects on the organs, for example by means of a magnet placed around the apparatus. The parameters of the control unit and also of the actuator can be adjusted by the physician after the implantation of the apparatus during the postoperative consultations using an advanced remote control.

The control of the contractile structure and more especially its opening can be achieved by a manual control of the control unit by means of a remote control to open and close the urethra. The remote control is preferably wireless. For the physician, the remote control can be designed to enable adjustments of the medical device (activation force, parameters of the pulsatory and alternately activation, test and diagnosis mode). An optical signal and/or vibration signal may be provided in order to show the patient the level of the battery status. Two different remote controls can be provided: a simple remote control for the patient and an advanced remote control for the healthcare professionals. The patient gets a simple remote control to open and close the contractile structure and to get few information like battery status and device status. The healthcare professionals have an advanced remote control that in addition allows to readjust the pressure and frequency, move the device into the examination mode as described below (motor will move typically 5 mm in the opposite direction of closing the contractile elements), reading implant parameters.

For emergency, the control unit may be controlled by means of a switch placed under the skin, which is activated by pressure on one or several buttons. Preferably, the switch comprises several buttons and the sequence for pressing the buttons is predetermined in order to avoid accidental opening of the structure.

Another alternative for safety is the automatic opening of the contractile elements after reaching a certain force (typically 5N) or pressure.

In other embodiments, the control of the contractile structure and more especially its opening can be achieved, by the physician or the patient himself, by a manual control of the contractile elements themselves by means of a releasing device designed to manually open the contractile structure. Such releasing device can be used if the patient lost the remote control or if a surgeon wishes to open the structure to endoscopically examine the patient or if a kidney stone has to be removed. This corresponds to the examination mode (motor will move typically 5 mm in the opposite direction of closing the contractile elements to totally open the contractile elements) allowing the examination with an endoscope without risk of damage of the urethra.

The medical device may further comprise sensing means selected from pressure, temperature and movement sensing means. Said sensing means can be fixed to the artificial contractile structure, may even form part of it, or may be separated from the support. For example, the medical device may comprise means to measure the pressure during the adjustment of the pressure applied to the organ by the contractile elements individually for a patient.

EXAMPLES

Figure 1:
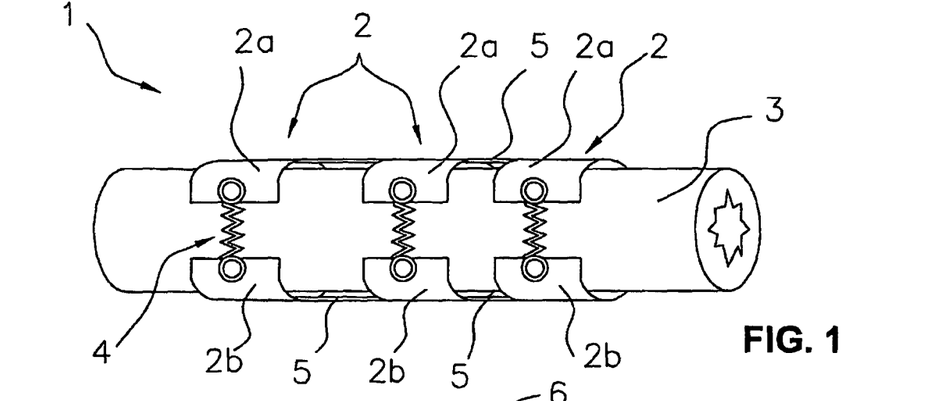
FIG. 1 is a side view of a first embodiment of an artificial structure used in the present invention, the fibers being inactivated.
Figure 2:
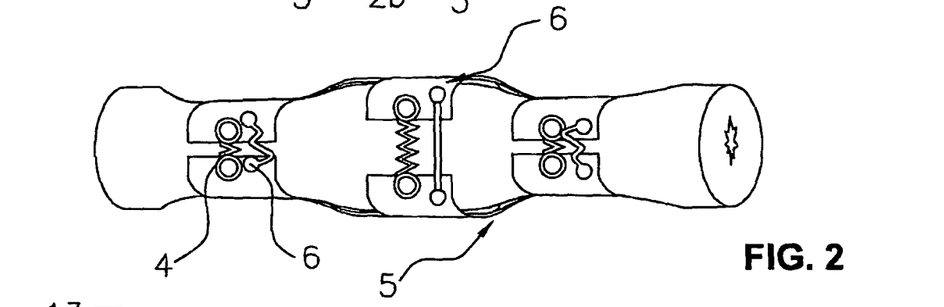
FIG. 2 is a side view of the structure of FIG. 1, the fibers being activated.

Referring to FIGS. 1 to 2, one embodiment of an artificial contractile structure 1, used to treat urinary incontinence, comprises three contractile elements 2 surrounding partially a hollow part 3 of the urethra, for example. In this example, each contractile element 2 comprises two separate parts 2a, 2b, linked to each other, and one each side, by a fiber 4 placed outside, so that the fiber 4 is not integrated in the parts 2a, 2b. More specifically, one each side of the parts 2a, 2b, one of the ends of a fiber 4 is fixed to a zone near the end of the part 2a, and the other end of said fiber 4 is fixed to a zone near the end of the part 2b, facing part 2a.

The contractile element 2 is made of silicon and the fiber 4 is made of Nitinol. Each fiber 4 is covered with elastic biocompatible materials for electrical and thermal insulation.

In other embodiment (not shown), the fibers 4 are placed in a box away from the organ to be contracted. The fibers 4 are replaced with cables, one end of the cables being connected to the part 2b of the element 2, the part 2a comprising a hole crossed by the cable. The other end of the cables is connected to the fibers placed in the box. The contraction of the fibers induces a force transmitted by the cable and applied on the part 2b of the elements 2 to close them.

The structure 1 further comprises flexible connecting elements 5 linking each part 2a, 2b of a contractile element 2 to respectively the part 2a, 2b of an adjacent contractile element 2. The flexible connecting element 5 is made out of elastic biocompatible material for keeping the contractile elements 2 in longitudinal position while allowing a rotational movement of each contractile element 2 one with respect to the other.

As shown in FIG. 2, the contractile element 2 further comprises a restricting element 6, fixed near each fiber 4, and designed to define a preload on the hollow part 3 and to limit an overexpansion of said fiber 4. More specifically, one of the ends of the restricting element 6 is fixed to a zone near one end of the part 2a of a contractile element 2, and the other end of the restricting element 6 is fixed to a zone near the part 2b, facing part 2a, of said contractile element 2.

In the medical device of the invention, the structure 1 may be used with an actuator controlled by a control unit comprising a microprocessor adapted to distribute current to fibers 4 and to drive the contraction of the fibers, preferably in order to pulsatory and alternately contract said fibers 4. There are also means for opening on demand said artificial contractile structure, used by the patient to inactivate all the fibers of the structure and open it, and an implantable source of energy, for example a rechargeable battery. A transcutaneous energy transfer supply can be developed for battery recharge. The apparatus can further comprise one or more sensing means selected from pressure, temperature and movement sensing means.

Each contractile element 2 forms an independently activatable gate, being able to constrict the corresponding region of the hollow part 3 to close it. Preferably, the contractile elements close in a pulsating and alternating manner, and independently of each other.

The length of the fiber is chosen so that the pressure of each fiber, when it is contracted, on the ends of the parts 2a, 2b is high enough so that the ends of the parts 2a, 2b come closer to each other. Then the contractile element applies a pressure to the hollow part to close it.

The structure 1 is placed and fixed around the hollow part 3. The contractile elements 2 and the fibers 4 are therefore distributed along the hollow part 3. In inactivated position, as shown by FIG. 1, the fibers 4 are in resting position and are not contracted. The region of the hollow part 3 around which the contractile element 2 has been placed is not compressed and then not closed.

When an electric current/voltage is applied to some fibers 4 by the control unit, the heated fiber 4 is activated and contracts, as shown by FIG. 2, in such a way as to reduce its length and then to move the ends of the parts 2a, 2b closer to each other, in order to reduce the diameter of the corresponding region of the hollow part 3, until it is closed.

As there are three contractile elements, there are three gates which can be independently, pulsatory and alternately activated in order to contract one or the other region around which the contractile element 2 has been placed, in a pulsating and alternating manner. This allows an alternate contraction along the urethra, several times an hour. Such a configuration avoids stressing of the underlying tissue followed by erosion and necrosis.

The control unit is designed to activate at least one fiber and therefore to contract at least one contractile element so that at least one region of the urethra is closed to avoid incontinence. The patient deactivates the device if necessary, so that each fiber is inactivated to open each region of the hollow part of the urethra, allowing the passage of the urine.

Moreover, if the device of the invention fails, there is no current in the fibers, which are therefore in the resting position. The structure 1 remains open. No surgery is necessary to allow the passage of the urine, for example.

Obviously, the device of the invention can be used with an actuator adapted to distribute current to fibers 4 and to drive the contraction of the fibers, on demand, without pulsatory and alternately contracting the fibers.

Obviously, the contractile element may be a single piece, with fibers fixed to each end of the piece.

Figure 3:
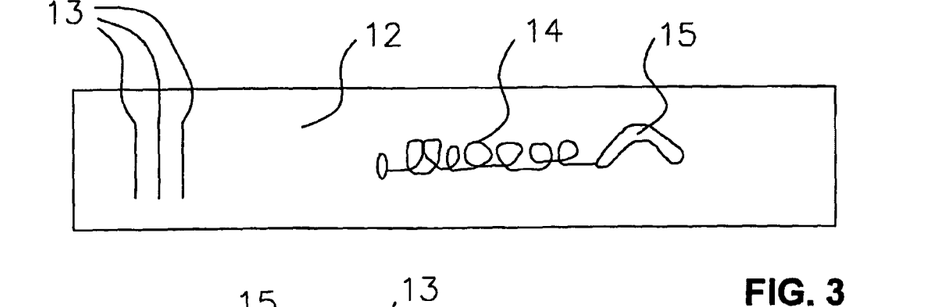
FIG. 3 represents another embodiment of a structure used in the present invention, unrolled.
Figure 4:
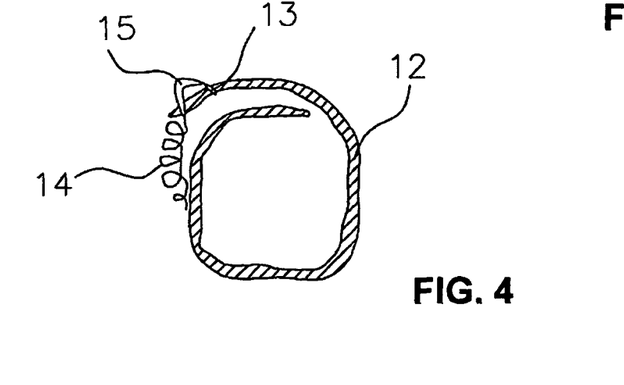
FIG. 4 is a cross-sectional view of structure of FIG. 3, rolled and closed.

Referring now to FIGS. 3 and 4, another embodiment of contractile element is shown. In this example, the contractile element is a band 12 which is designed to surround at least one time the hollow part of the organ to be contracted in such a way that the ends of the band 12 overlap each other. A fiber 14 is fixed to a first zone of the band 12 and comprises, to its free end, a hook 15 designed to be fixed to a complementary hook 13 which is fixed to a second zone of the band 12.

The band comprises three hooks 13 for the fixation of the fiber 14, in order to adapt the length of the structure to urethra diameter.

The hooks 13 for the fixation of the fiber 14 are placed for example near the end of the band 12 in such a way that, when the band 12 is rolled, the fiber 14 crosses the overlap zone to close it.

The band 12 is made of silicon and the fiber 14 is made of Nitinol. The fiber 4 is covered with elastic biocompatible materials for electrical and thermal insulation.

When the fiber 14 is contracted, the zones to which the fiber 14 is fixed come closer to each other, in such a way that one end of the band 12 slides over the other end of said band 12, and in order to reduce the diameter of the contractile element.

The band 12 is used as contractile element 2 described above.

Figures 5, 6:
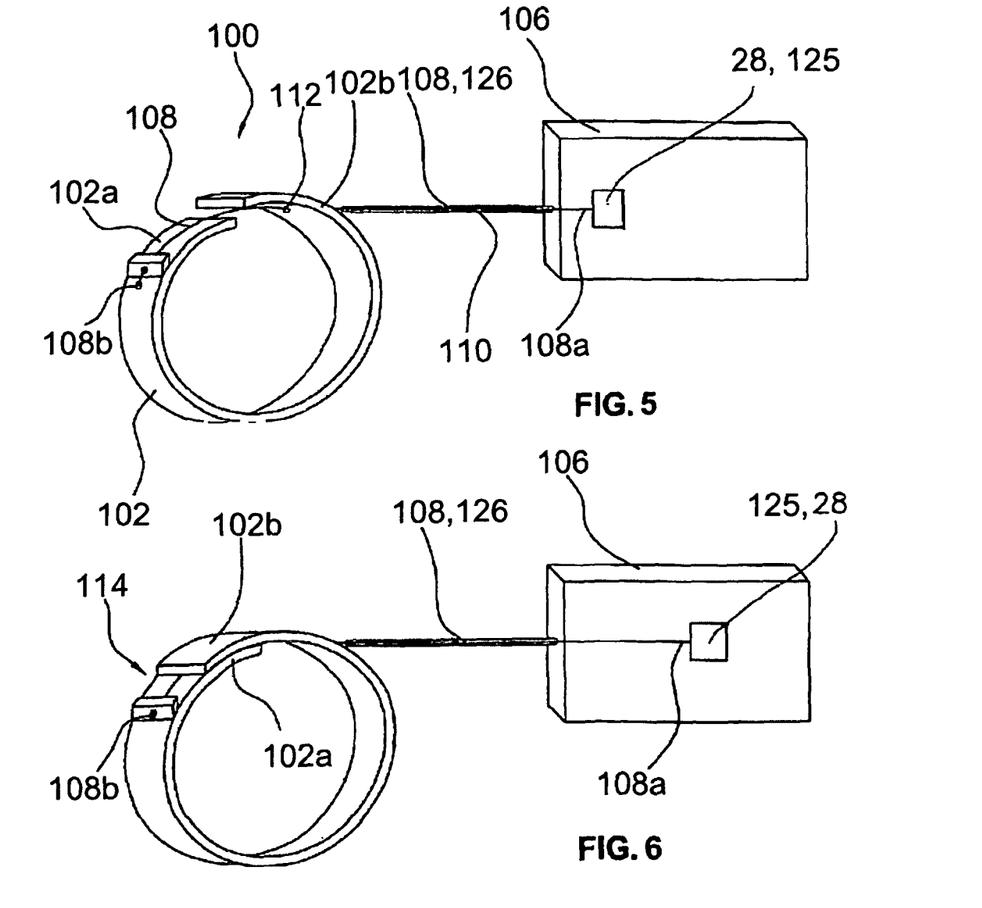
FIG. 5 is a schematic view of another embodiment of the device according to the present invention, the contractile element being in resting position.
FIG. 6 is a schematic view of the device of FIG. 5, the contractile element being in activated position.

Referring now to FIGS. 5 and 6, another embodiment of the medical device of the present invention is shown, used to treat urinary incontinence. For simplification of the drawings, only one contractile element 100 is shown. But the medical device of the invention comprises a contractile structure comprising at least two contractile elements 100 adapted to be placed around the hollow part of the urethra, for example, and linked by connecting elements as the connecting elements shown by FIGS. 1 and 2.

The contractile element 100 comprises a band 102 designed to surround at least one time the hollow part of the organ to be contracted. The band 102 is made of silicone, PTFE, PLA, PUR, PMMA, (POM), HDPE LDPE or combination thereof to reduce the friction when the band wraps closely around the organ. Other appropriate material, such as metal, can be used.

The medical device comprises also an actuator placed in a box 106 away from the organ to be contracted. Such an actuator can be contractile fibers linked to the contractile element 100 by a cable 108 or an actuator as shown by FIG. 7 or by FIG. 9.

Figure 7:
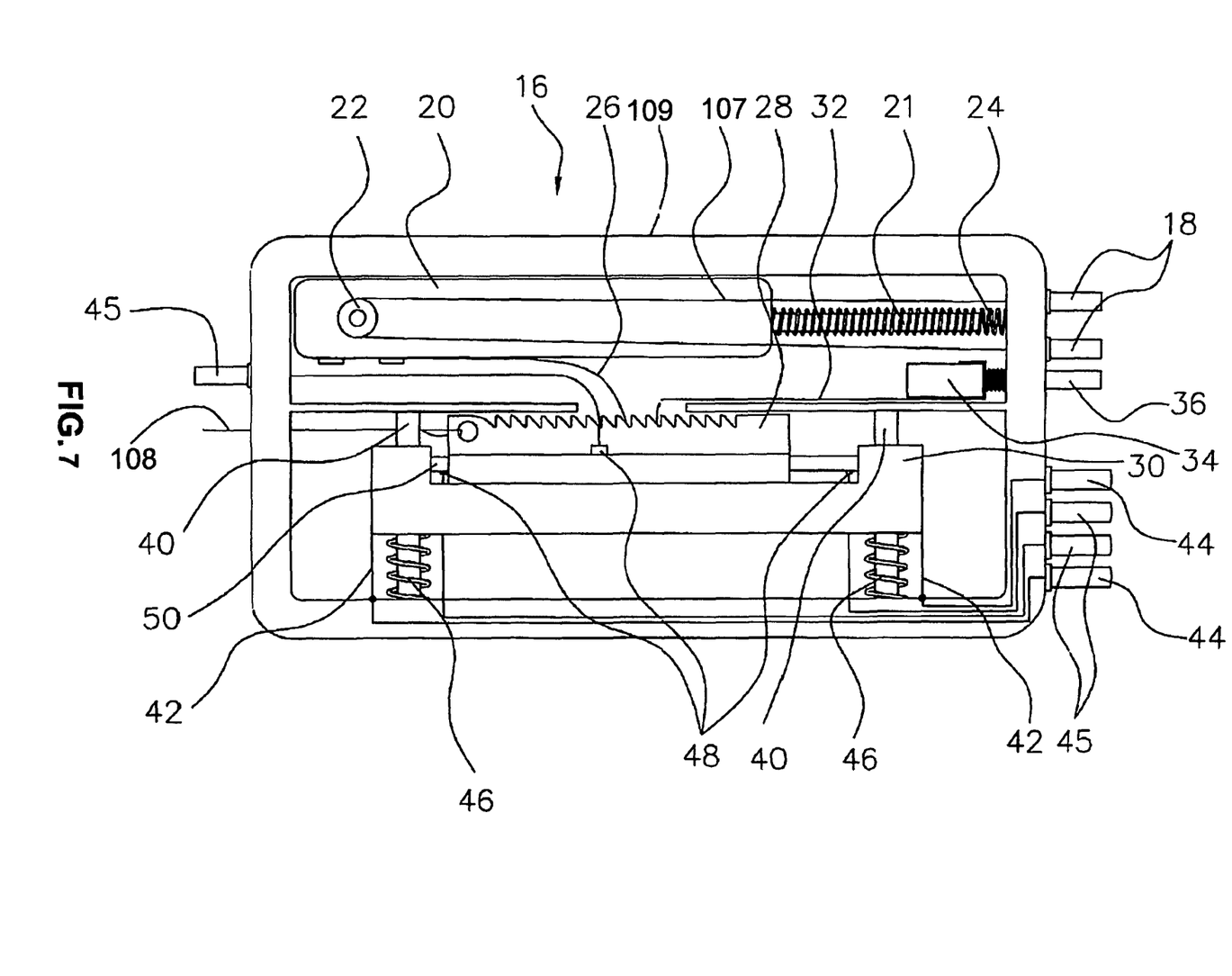
FIG. 7 is a schematic view of an embodiment of actuator used in the device of FIGS. 5 and 6.

Referring now to FIG. 7, an embodiment is shown of an actuator 16 used to activate each contractile element of a structure of the invention, for which the fibers are separated from the support. In this example, said actuator 16 comprises fibers 107, made of a contractile material which contracts when heated, as Nitinol.

The ends of the fibers 107 are secured to a box 109 which comprises electrical connections 18 to supply electrical energy to the fibers 107 for their contraction.

The actuator 16 further comprises an oscillating device 20 slidably mounted on a fixed shaft 21. The oscillating device 20 comprises also a pin 22, around which the fibers 107 wrap, in such a way that the fibers 107 pull the oscillating device 20 when they contract. The oscillating device 20 comprises also a return spring 24 for its return to its initial position when the fibers 107 do not contract any more and recover their length of their resting position. Therefore, the oscillating device 20 can oscillate under the effect of repeated modifications of the length of the fibers which contract or not, driven by the control unit.

In such a way as to convert its oscillations into contracting movements, said oscillating device 20 comprises a metallic pushing strip 26, which is curved in the direction of a toothed mobile element 28, as a rack.

The rack 28 is linked to the contractile element 100 of FIGS. 5 and 6 by means of a cable 108, which is protected by a coaxial sheath 110. One end 108a of the cable 108 is connected liquid tight and may be reversibly linked to the rack 28. The other end 108b of the cable 108 is linked liquid tight and may be reversibly linked to one end 102a of the band 102. The other end 102b of the band 102 comprises a hole 112 through which the cable 108 runs.

Soft foam could be placed in the space 114 between the band 102 and the cable 108 to avoid tissue in-growth between the cable 108 and the contractile element 100. Alternatively, the sliding surfaces of the band could be modified to prevent tissue in-growth, for example by coating.

The rack 28 is slidably mounted on a longitudinal rod 50 fixed to a supporting part 30. Said rack 28 is designed to cooperate with the pushing strip 26 in such a way that the pushing strip 26 pushes the rack 28 in a direction between an initial position and a final position, such positions corresponding for example respectively to the resting position and the activated position of the corresponding contractile element.

The actuator 16 comprises also retaining means which are designed to cooperate with the rack 28 and to prevent said rack 28 from going back in an opposite direction. Such retaining means are for example a hook or a jumper spring 32, fixed to a support 34 and designed to cooperate with the teeth of the rack 28. The jumper spring 32 is flexible so that, when the rack 28 moves, the teeth of the rack 28 lift the jumper spring 32, which then drops between two other teeth to hold the rack 28 in its position.

The support 34 is connected to the box 109 with a screw 36 for the set up of the jumper spring 32.

The actuator 16 comprises also releasing means designed to separate the pushing strip 26 and the jumper spring 32 from the rack 28 in such a way that the rack 28 comes back into its initial position.

For that purpose, the supporting part 30 is slidably mounted on two axial rods 40 fixed to the box 109. The supporting part 30 is designed to be movable along said rods 40, in such a way that the supporting part 30 and the rack 28 are able to move away from the pushing strip 26 and the jumper spring 32 when the support part 30 is under the effect of the releasing means. In this embodiment, said releasing means are Nitinol fibers 42, secured to the supporting part 30 and the box 109. When the rack 28 has to come back into its initial position, the fibers 42 are heated, so that they contract in order to pull on the supporting part 30 and move it away from the pushing strip 26 and the jumper spring 32. The box 109 comprises electrical connections 44 to supply electrical energy to the fibers 42 for their contraction.

The supporting part 30 comprises also two return springs 46, placed around the rods 40, for its return in the position for which the fibers 42 are not contracted.

The actuator 16 further comprises sensors 48 designed to indicate the exact position of the rack 28 to the control unit, and therefore the position of the corresponding contractile element: totally open, half open, totally closed. The box 109 comprises electrical connections 45 to supply electrical energy to the sensors 48.

In FIG. 5, the fibers 107 have not been contracted, the rack 28 is in its initial position and the contractile element 100 is in a resting position, the band 102 being loosely wrapped around the organ.

When an electric current/voltage is applied to the fibers 107 by the control unit through the connections 18, the heated fibers 107 are activated and contract in such a way as to reduce their length compared to their length in the resting position. When the fibers 107 contract, they pull the oscillating device 20, which moves, in such a way that the pushing strip 26 moves also and pushes on one tooth of the rack 28.

Then, the rack 28, moving to its final position, pulls on the cable 108, which pulls on the corresponding contractile element 100 to close it.

More especially, the rack 28, by moving to its final position, moves the end 108a of the cable 108 into the box 109. So that the other end 108b of the cable 108 is moved as the same way. By moving, the end 108b of the cable pulls on the end 102a of the band 102 which slides under the other end 102b to close the contractile element 100.

At the same time, the jumper spring 32 cooperates with the teeth of the rack 28 to prevent it from going back in the opposite direction.

The control unit is designed to generate impulsions of current so that the fibers 107 contract and come back in their resting position several times, in such a way that the oscillating device 20 oscillates under the effect of the repeated modifications of the length of the fibers. At each oscillation, the pushing strip 26 pushes on one tooth of the rack 28, which pulls on the cable 108, until said rack 28 is in its final position, and until the contractile element is closely wrapped around the organ to constrict it. The contractile element 100 is then in an activated position as shown by FIG. 6.

In this embodiment, the fibers do not need to be heated to contract in order to maintain the contractile element in its activated position, because the jumper spring 32 retains the rack 28 in its final position.

When the contractile element 100 has to come back in its resting position, the control unit supplies electrical energy to the fibers 42 by the connections 44. The fibers 42 contract and pull on the supporting part 30. Therefore, such supporting part 30 and the rack 28 move away from the pushing strip 26 and the jumper spring 32. In such a way, the rack does not cooperate with the pushing strip 26 and the jumper spring 32 any more, so that the rack 28 comes back in its initial position. The cable 108 is not pulled by the rack 28 any more in such a way that the contractile element comes back to its resting position.

Figure 8:
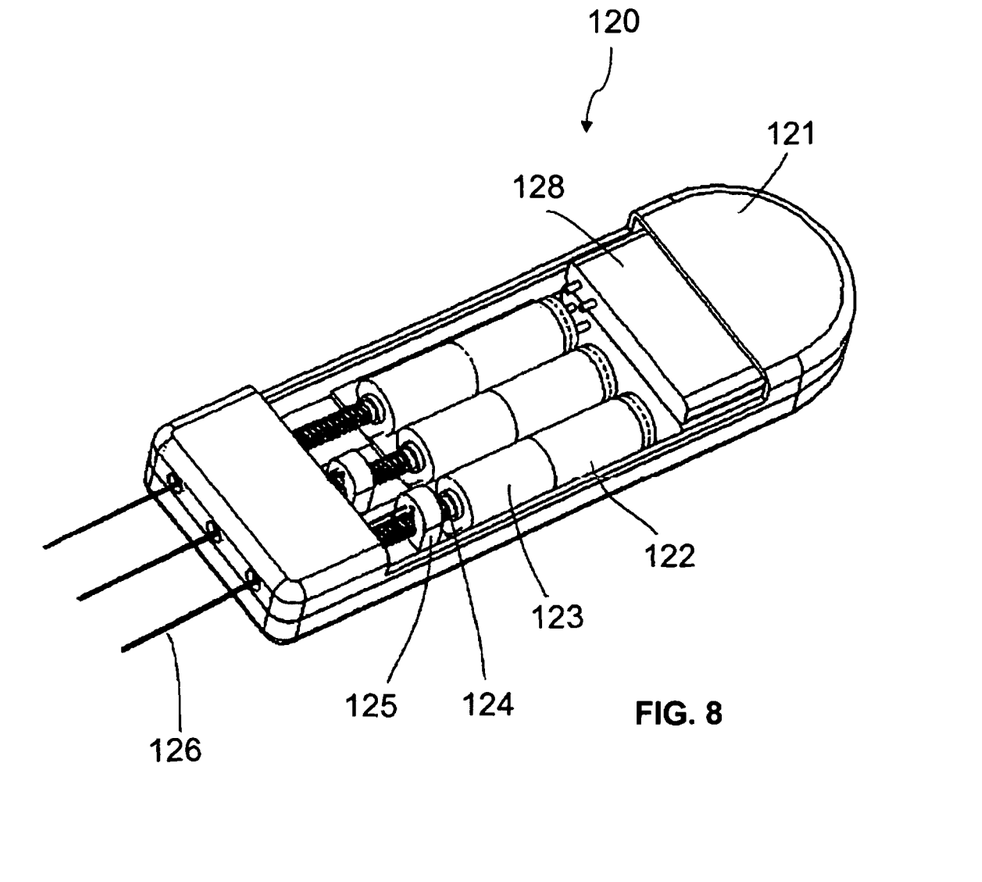
FIG. 8 is a schematic view of another embodiment of actuator used in the device of FIGS. 5 and 6.

Referring now to FIG. 8, an embodiment is shown of a control unit 120 used to control and activate for example three contractile elements 100 as shown in FIGS. 5 and 6. The control unit 120 is placed in a box 121 made of polymer or titanium. The control unit 120 comprises three actuators, each having an electromotor comprising an electric motor 122, a gearhead 123 connected to said motor 122, a lead screw 124 cooperating with said gearhead 123, and a nut 125 mounted on said lead screw 124. The nut 125 is connected to a cable 126 that transmits the force to the corresponding contractile element 100 to close or open it. The cable 126 is surrounded by a silicon tube. The cable is made of stainless steel, titanium or polymer.

Each nut 125 moves along the corresponding lead screw 124 to close or open the corresponding contractile element 100.

The control unit 120 comprises also a printed circuit board to control the actuators and batteries 128, for example rechargeable batteries. A percutaneous energy transfer supply can be developed for battery recharge.

Figure 10:
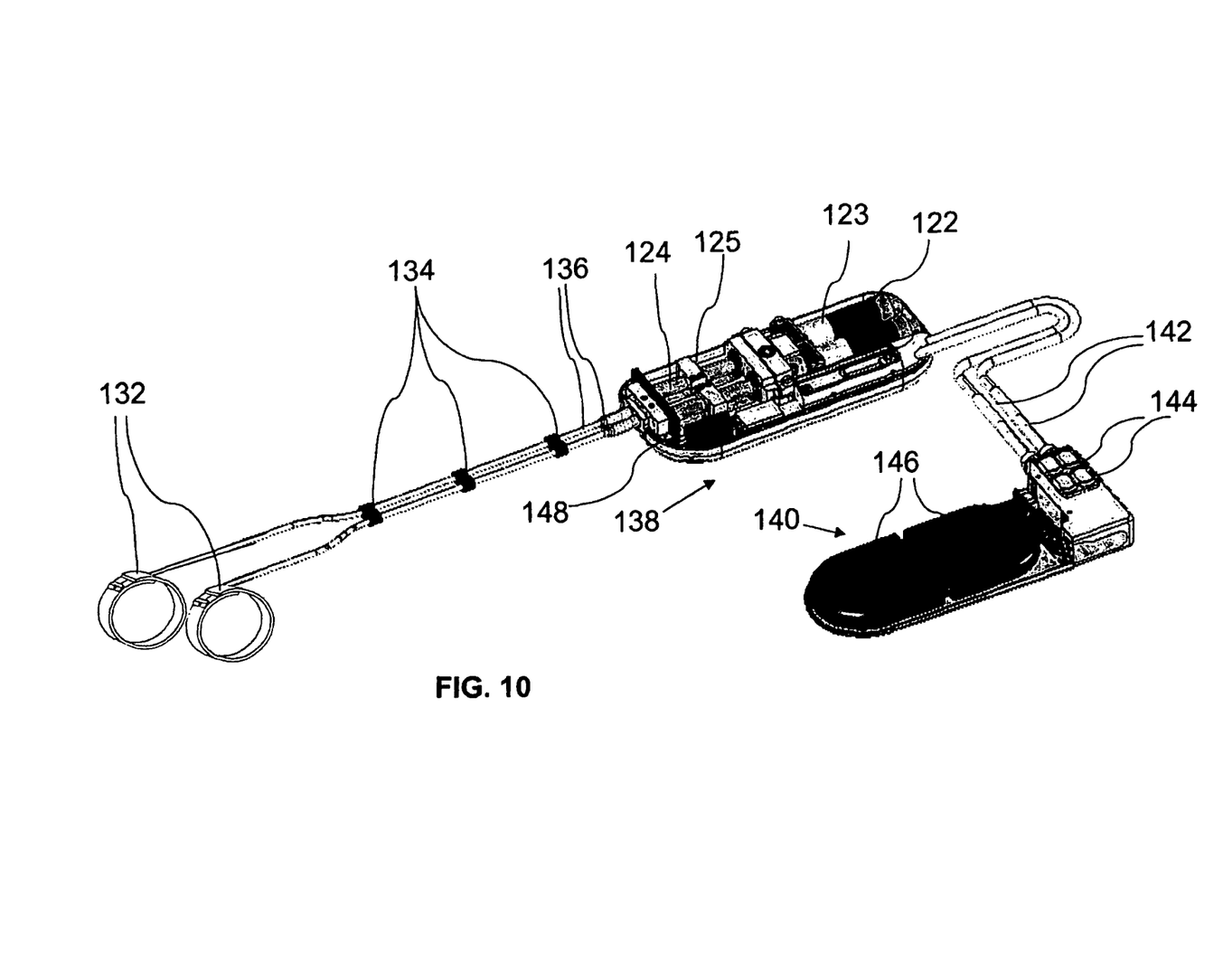
FIG. 10 represents a schematic view of another embodiment of the device according to the invention.

In another embodiment as shown by FIG. 10, two adjacent contractile elements 132 are indirectly connected by using bars 134, said bars being connecting elements fixed around the transmission means and used to merge said two adjacent transmission means, i.e. the two adjacent cables 136.

In this embodiment, the control unit 138 comprises two actuators, each having an electromotor comprising an electric motor 122, a gearhead 123 connected to said motor 122, a lead screw 124 cooperating with said gearhead 123, and a nut 125 mounted on said lead screw 124. The nut 125 is connected to each cable 136 that transmits the force to the corresponding contractile element 132 to close or open it. Each nut 125 moves along the corresponding lead screw 124 to close or open the corresponding contractile element 132.

The control unit 138 is separated from the energy source. The energy source is in the power supply unit 140 that is connected to the control unit 138 by electric cables 142, which are easily detachable by using connectors 144. The energy source comprises two implantable primary 146 (i.e. non-rechargeable) batteries, each having a lifetime of at least 4 years for a volume of 3.7 cm$^3$.

A travel sensor is provided in such a way that the control unit 120 or 138 knows the exact position of the nuts 125 and therefore the position of each contractile element 100 or 132. It is also needed for the readjustment of the force.

When an electric current is applied to an electromotor by the control unit 120 or 138, the corresponding lead screw 124 rotates in such a way that the corresponding nut 125 is moving along the corresponding lead screw 124. If the nut 125 moves away from the contractile element 100 or 132, the nut 125 pulls on the corresponding cable 126 or 136, which pulls on the corresponding contractile element 100 or 132 to close it.

In this embodiment, no energy is needed to maintain the contractile element 100 or 132 in its activated position. When the contractile element 100 or 132 has to come back in its resting position, the control unit 120 or 138 supplies electrical energy to the electromotor, in such a way that the lead screw 124 rotates in the opposite direction. The nut 125 comes closer to the contractile element 100 or 132. Then, the cable 126 or 136 is not pulled by the nut 125 any more in such a way that the contractile element 100 or 132 comes back to its resting position.

The control unit 120 or 138 is adapted to distribute current to each electromotor, preferably in order to pulsatory and alternately contract the contractile elements 100 or 132.

In case of power loss, the control unit comprises a capacitor 148 which has enough energy stored to apply to the electromotors and to open the contractile elements 100 or 132.

There are also means for opening on demand said artificial contractile structure, used by the patient to inactivate the actuators and open the contractile elements. The device can further comprise sensing means selected from pressure, temperature and movement sensing means.

As there are several contractile elements, there are several gates which can be independently, pulsatory and alternately activated in order to contract one or the other region around which the contractile elements 100 or 132 have been placed, in a pulsating and alternating manner. This allows an alternate contraction along the urethra for example, several times an hour. Such a configuration avoids necrosis of the underlying tissue.

The control unit is designed to activate at least one actuator and therefore to activate at least one contractile element so that at least one region of the urethra is closed to avoid incontinence. The patient deactivates the device if necessary, so that each actuator is inactivated to open each region of the hollow part of the urethra, allowing the passage of the urine.

The control of the contractile structure and more especially its opening can be achieved, by the physician or the patient himself, by a manual control of the contractile elements themselves by means of a releasing device designed to manually open the contractile structure.

Obviously, the device of the invention can be used with a control unit adapted to drive the contraction of the contractile elements, on demand, without pulsatory and alternately contracting said contractile elements.

The operating time of the medical device as shown by FIG. 10 was tested for different travels of the nut 125 and for different cycle times. The travel is the distance covered by the nut 125 moving along the lead screw 124 in such a way that the contractile element moves between its resting and activated positions. A cycle time comprises movement of the nut for closing the contractile element, time for which the contractile element is closed, movement of the nut for opening the contractile element and time for which the contractile element is opened.

The travels were 10 mm, 8 mm and 5 mm. The cycle times were 10 minutes, 20 minutes and 30 minutes.

The electromotor comprised the motor 08GS61 from Portescap, the lead screw pitch is 1.80 mm and the diameter 2.00 mm; gear ratio is 16.

The control unit comprises as source of energy two primary batteries of 1.1 Ah, with an assumed shelf life of 1 year.

The pressure applied by the contractile element on the organ was 1.5 N.

Figure 9:
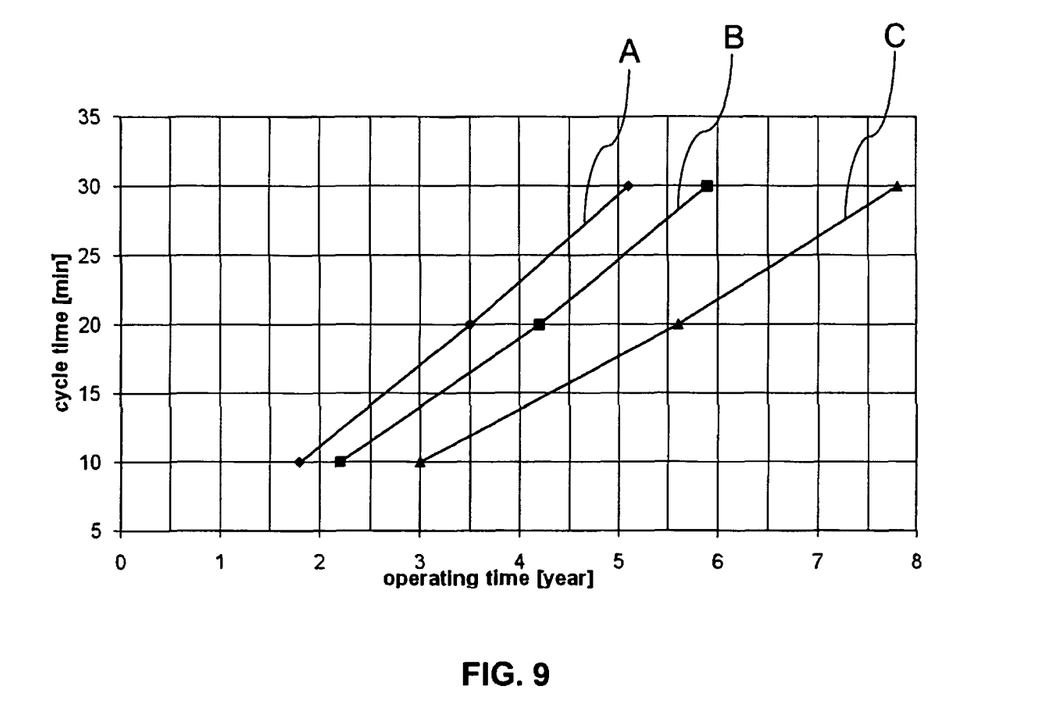
FIG. 9 represents the cycle time as a function of the operating time for a device of the invention using an electromotor.

The results are shown by FIG. 9, which represents the cycle time as a function of the operating time for different travels for a travel of the nut of 10 mm (curve A), a travel of 8 mm (curve B) and a travel of 5 mm (curve C). FIG. 9 shows that the medical device of the invention allows to use primary batteries enabling to obtain an operating time of 1.8 years to 7.8 years.

The same medical device was compared with a similar medical device but using a rechargeable battery of 200 mAh, and with a medical device using an actuator as shown by FIG. 7 with contractile fibers and the same rechargeable battery of 200 mAh.

The travel of the nut was 10 mm and the pressure applied by the contractile element on the organ was 1.5 N.

In the first case, the cycle time was 10 minutes and in the second case, the cycle time was 30 minutes.

The results are shown in the Table below:

| Type of power supply | Volume | power supply | Actuator system | Typical operating time before exchange/recharge | |
|---|---|---|---|---|---|
| | | | | cycle time = 10 min. | cycle time = 30 min. |
| Rechargeable Battery 200 mAh | 3.3 ml + | TET | Figure 7 with Nitinol fibers | 1 day | 3 days |
| Rechargeable Battery 200 mAh | 3.3 ml + | TET | Figure 8 with electromotor | 2 months | 5.5 months |
| Primary Battery 2 × 1.1 Ah | 7.4 ml | | Figure 8 with electromotor | 1.8 years + 1 year shelf life | >5 years + 1 year shelf life |

The Table shows that the medical device of the invention using an electromotor and a primary battery has an operating time of more than 5 years before exchange of the battery, with a cycle time of 30 minutes, and of 2 years with a cycle time of 10 minutes.

Moreover, such a medical device allows applying minimal pressure to the tissues thereby avoiding tissue necrosis and damage, even if each contractile element applies a pressure at a frequency of 30 to 45 minutes alternately with the other contractile elements. That means that every contractile element is closed for 30 to 45 minutes alternately with the other contractile elements. A device as AMS 800 shows erosion because the device is closed for about 6 to 8 hours per night and during the day for about 4 hours, assuming that the patient goes every 4 h to the toilet.

The invention claimed is:

1. A medical device comprising:
   an artificial contractile structure comprising at least two contractile elements configured to contract an organ such that each of said contractile elements are in a resting or in an activated position, independently of the position of each other, the activated position being defined with said contractile element constricting the organ and the resting position being defined with said contractile element not constricting the organ; and
   at least one actuator configured to activate said contractile structure,
   wherein each contractile element is connected to an adjacent contractile element, while remaining flexible with respect to the other,
   wherein said at least one actuator is separated from the artificial contractile structure, the at least one actuator comprising
      transmission means linked to the contractile elements and configured to transmit to the contractile elements a force induced by the actuator, and
      at least one electromotor linked to said transmission means, the transmission means being designed to transmit to the contractile elements a force induced by said electromotor, said electromotor comprising
an electric motor,
a gearhead connected to said motor,
a lead screw cooperating with said gearhead,
and a nut mounted on said lead screw and linked to said transmissions means.

2. The medical device according to claim 1, further comprising at least two actuators, each of said actuators being associated with one of said contractile elements and configured to activate said associated contractile element.

3. The medical device according to claim 2, wherein each actuator comprises fibers made of a contractile material and fixed to each of said contractile elements.

4. The medical device according to claim 1, wherein said actuator comprises at least one fiber made of a contractile material and linked to said transmission means, the transmission means being designed to transmit to the contractile elements a force induced by at least one contraction of the fiber.

5. The medical device according to claim 1, wherein the actuator further comprises sensors configured to indicate a position of the nut.

6. The medical device according to claim 1, wherein said transmission means are mechanical, hydraulic, electromechanical or pneumatic.

7. The medical device according to claim 1, wherein each contractile element comprises a band which surrounds at least partially the organ to be contracted, and
wherein the transmission means is configured to be fixed to one end of the band and to pull the band in such a way that the band constricts the organ when the force induced by the actuator and transmitted by the transmission means is applied on said contractile element.

8. The medical device according to claim 7, wherein the band comprises at one end a point for fixing the transmission means and at another end a hole crossed by the transmission means.

9. The medical device according to claim 1, wherein the contractile elements are each flexible so that each of the contractile elements is configured to move longitudinally no more than 5 mm, to each direction from an adjacent contractile element, and so that the contractile element moves according to a transversal rotation no more than 30° to each side from an adjacent contractile element.

10. The medical device according to claim 9, wherein each of the contractile elements is configured to move longitudinally no more than 3 mm to each direction from an adjacent contractile element, and
the contractile element moves according to a transversal rotation no more than 20° to each side from an adjacent contractile element.

11. The medical device according to claim 1, further comprising a first flexible connecting element configured to link each contractile element to an adjacent contractile element, said first connecting element being made out of elastic biocompatible material to keep said contractile elements in a longitudinal position while allowing a rotational movement of each contractile element, one with respect to the other.

12. The medical device according to claim 1, wherein two adjacent transmissions means are merged such that two corresponding adjacent contractile elements are indirectly connected.

13. The medical device according to claim 12, further comprising at least one second connecting element configured to merge the adjacent transmission means of two adjacent contractile elements.

14. The medical device according to claim 1, wherein each said contractile element is separated from an adjacent contractile element no less than 1 mm to 2 cm to avoid overcompression.

15. The medical device according to claim 14, wherein each said contractile element is separated from an adjacent contractile element no less than 2 mm to 1 cm.

16. The medical device according to claim 1, wherein the artificial contractile structure comprises between 2 and 8 contractile elements, so that said structure makes an overall length comprised between 20 mm and 50 mm.

17. The medical device according to claim 1, further comprising a control unit which is configured to activate the actuator such that each contractile element is activated pulsatory and alternately relating to the other contractile elements.

18. The medical device according to claim 17, wherein the actuator is configured so that the contractile element applies, in a pulsating and alternating manner, a pressure on an organ to be contracted during a period comprised between 30 seconds and 90 minutes.

19. The medical device according to claim 18, wherein the actuator is configured so that the contractile element applies, in a pulsating and alternating manner, the pressure on an organ to be contracted during a period comprised between 30 seconds and 60 minutes.

20. The medical device according to claim 1, further comprising a source of energy.

21. The medical device according to claim 20, wherein the source of energy comprises at least one implantable rechargeable battery with an implantable antenna and an external battery.

22. The medical device according to claim 20, wherein the source of energy is at least one implantable primary battery.

23. The medical device according to claim 1, further comprising at least one remote control.

24. The medical device according to claim 23, further comprising two different remote controls, one tiny remote control for the patient and an advanced remote control for healthcare professionals.

* * * * *